United States Patent [19]

Baker et al.

[11] Patent Number: 4,486,536
[45] Date of Patent: Dec. 4, 1984

[54] SPECIMEN SLIDE FOR OCCULT BLOOD TESTING

[75] Inventors: Josefina T. Baker, Cupertino; Paul J. Lawrence, Campbell; Charles W. Townsley, San Jose, all of Calif.

[73] Assignee: Smithkline Diagnostics, Inc., Sunnyvale, Calif.

[21] Appl. No.: 409,753

[22] Filed: Aug. 19, 1982

Related U.S. Application Data

[63] Continuation-in-part of Ser. No. 382,908, May 28, 1982, abandoned.

[51] Int. Cl.³ .................... G01N 21/78; G01N 33/72
[52] U.S. Cl. ........................................ 436/66; 422/56; 422/58; 422/61
[58] Field of Search .................. 422/56, 57, 58, 61; 436/66

[56] References Cited

U.S. PATENT DOCUMENTS

| | | | |
|---|---|---|---|
| 2,990,338 | 6/1961 | Gibson | 422/56 X |
| 4,063,894 | 12/1977 | Ogawa et al. | 422/56 X |
| 4,077,772 | 3/1978 | Geissler et al. | 436/66 |
| 4,132,527 | 1/1979 | Maekawa et al. | 422/56 X |
| 4,260,393 | 4/1981 | Gibson | 436/66 |
| 4,277,250 | 7/1981 | Melnick et al. | 436/66 |
| 4,308,028 | 12/1981 | Elkins | 422/56 X |
| 4,333,734 | 6/1982 | Fleisher | 436/66 |
| 4,365,970 | 12/1982 | Lawrence et al. | 436/66 |

OTHER PUBLICATIONS

Layne et al., Chemical Abstracts, vol. 95, 1981, No. 95:76337x.
*The Merck Index of Chemicals and Drugs,* 7th Edition, Merck & Co., N.J., 1960, p. 266.
Layne et al., Annals of Internal Medicine, 1981, 94:774-776.
Sudlow et al., The New England Journal of Medicine, Jun. 25, 1981, p. 1608, "Pitfalls of Hemocult Testing of Gastric Aspirates".

*Primary Examiner*—Arnold Turk
*Attorney, Agent, or Firm*—Joseph A. Marlino; Stuart R. Suter; Alan D. Lourie

[57] ABSTRACT

A method and novel absorbent substrate for determining the presence of occult blood in gastric fluid. The substrate is acid treated and contains guaiac. The method includes the addition of the gastric fluid to the acid treated guaiac substrate which is developed with a buffered developing solution. Preferably the substrate is an acid treated sheet of absorbent paper and the developing solution is an aqueous buffered solution of hydrogen peroxide.

6 Claims, 3 Drawing Figures

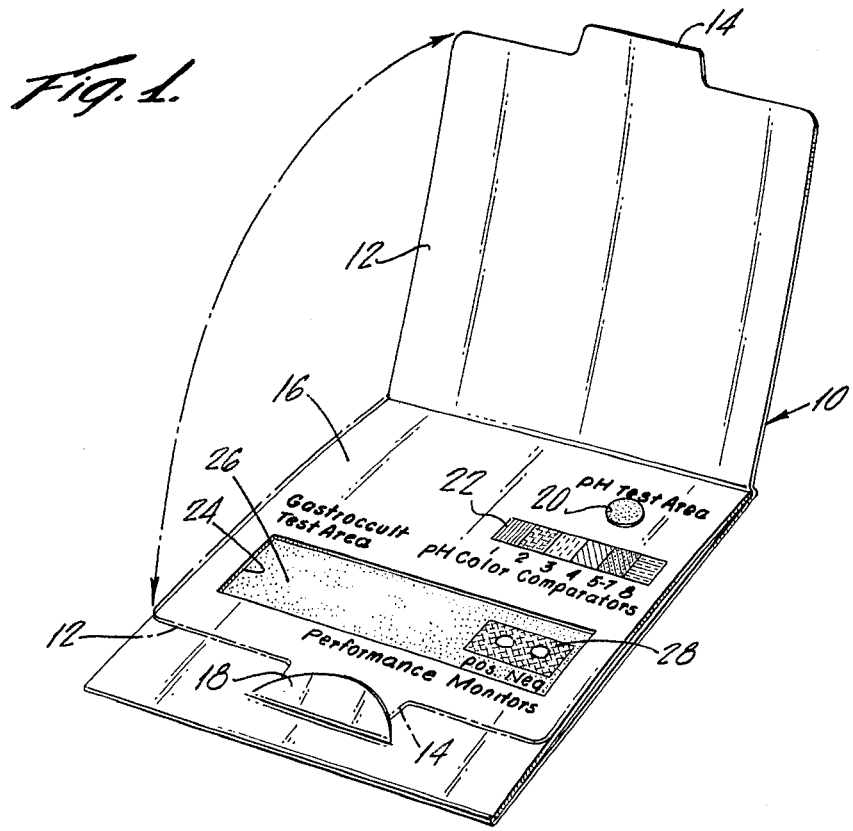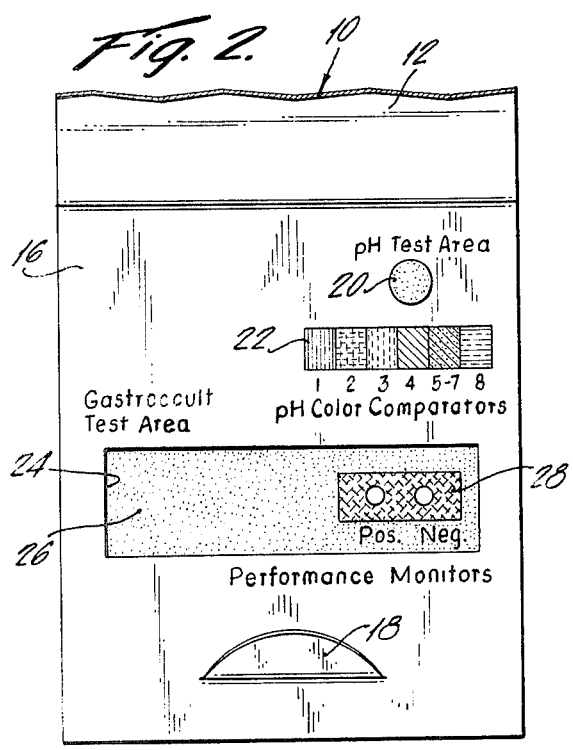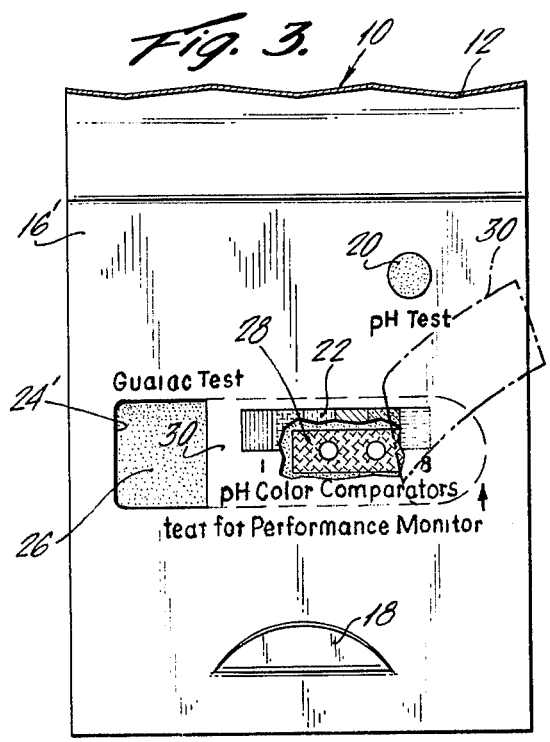

SPECIMEN SLIDE FOR OCCULT BLOOD TESTING

This application is a continuation-in-part application of co-pending Ser. No. 382,908, filed May 28, 1982, now abandoned.

Specimen test slides and procedures for detecting occult blood in fecal matter are well known. For example, U.S. Pat. No. 3,996,006 discloses slides having a substrate consisting of a specimen receiving sheet between a front panel and a rear panel with one or more openings in the front panel and an opening in the rear panel and pivotal covers to cover these openings. Typically, in the case of a test for occult blood in feces, the specimen receiving sheet is absorbent paper impregnated or printed with guaiac and a developing solution such as a peroxide solution is applied through the opening in the rear panel. One such test slide is sold under the trademark of "Hemoccult".

Briefly, the test procedure is as follows. A sample of fecal matter is smeared onto the guaiac paper through an opening of the front panel. The panel is then covered and the flap of the rear panel is opened. A developing solution such as hydrogen peroxide is applied to the guaiac paper via the corresponding opening in the rear panel. If blood is present in the fecal matter, the guaiac reaction will color the paper blue. The blue color is due to the hemoglobin catalyzed oxidation of the guaiac.

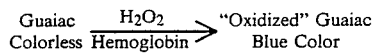

$$\text{Guaiac Colorless} \xrightarrow[\text{Hemoglobin}]{\text{H}_2\text{O}_2} \text{"Oxidized" Guaiac Blue Color}$$

One of the limiting characteristics of the guaiac test is that the hemoglobin catalyzed blue color formation is pH dependent. The developing solution does not operate reproducibly below a certain pH. The pH range for the successful performance of the above known system is from about 4.0 to 7.0 with the optimum pH being from 5.5 to 6.0. Thus, if hemoglobin is applied to the guaiac treated substrate in a medium that differs significantly from the optimum pH, little or possibly no color will be detected.

Due to the above disadvantage of the present slide, it is not designed for testing the presence of occult blood in specimens having a low pH such as gastric fluid which can have a pH below 2. Detection of compounds not normally present in gastric contents, specifically the presence of occult blood, is of clinical significance. Blood in gastric contents may originate from many sources including blood swallowed subsequent to trauma outside the gastrointestinal tract and gastrointestinal bleeding. In some pathological conditions, such as carcinoma of the stomach, peptic ulcer, and gastritis, blood may be present in the stomach. Ingestion of alcohol and various drugs such as aspirin, other analgesics and corticosteroids, can cause erosions in the stomach mucosal cells and eventual gastric bleeding. Gastric erosions and subsequent bleeding have also been recorded in patients admitted to hospitals for treatment of critical injuries or burns. This type of erosion may appear within 24 hours of the original trauma and can result in acute life-threatening gastric hemorrhage. The importance of this unexpected early detection of occult blood in the gastrointestinal tract would help in diagnosing any of the above conditions at an early stage while they can be treated more effectively.

It is therefore an object of this invention to provide a specimen test slide which will not be effected by variations in sample or specimen pH and could be employed for specimens other than fecal matter.

It is also an object of this invention to provide a fast, convenient qualitative test to aid in the diagnosis of gastrointestinal conditions by the early detection of occult blood in gastric fluids.

It is a further object of this invention to provide a specimen test slide which would eliminate false-positive reactions due to the presence of peroxidases, iron, copper or chemicals such as cimetidine.

Previous attempts have been made to stabilize the guaiac impregnated paper or test strip against pH variations and interfering substances such as peroxidases. German Offenlegungschrift 2,716,060 discloses the incorporation of buffering agents or chelating agents in the guaiac paper to overcome the above stated problems. The most critical need for buffering is when the media tested differ greatly from optimum pH such as in gastric fluids, or when small amounts of catalyst such as hemoglobin are to be detected.

Unexpectedly, it was discovered that when the buffering agents were placed in the developing solution and not impregnated in the guaiac paper as disclosed in the art, the specimen test slide is not effected by variations in sample or specimen pH and false positive reactions due to the presence of peroxidases, metal ions and cimetidine were eliminated.

Several major advantages result in buffering the developing solution instead of impregnating the guaiac paper with buffers. The amount of buffering agents that could be applied to the guaiac paper is limited due to the absorbency of the paper. Therefore, when strong buffering is needed it would be more effective to buffer the developer. It would also be difficult to get an even distribution of buffers on the paper. By buffering the developer, the pH is not limited to the pH of the substrate, i.e., the pH can be changed. Once the paper is impregnated the pH is well defined and limited. A heavy salt concentration on the paper would also affect other reagents and change the physical properties of the paper itself. By buffering the developer solution there would be no change in the manufacturing procedure of the specimen test slide. This approach is very cost effective.

Most advantageous results were obtained with the combined use of acid treated guaiac paper and a buffered developer. It was discovered that acid treatment of the guaiac paper eliminated false positive tests with cimetidine and decreased interference from peroxidases. Further, unexpectedly, the acid in the guaiac paper prevents the guaiac from turning blue during storage when atmospheric oxidation may take place. The buffered developer is needed to permit hemoglobin detection under the acidic conditions present in the guaiac. This is illustrated by the results of the following experiments.

Samples of synthetic gastric fluid containing 0.05 mg. of hemoglobin and 30 mg. of cimetidine per ml. were prepared. 25 μl. samples were applied to "Hemoccult" slides and developed with buffered and unbuffered developers. The "Hemoccult" slides were then acidified by acid treatment of the guaiac paper prior to application and development of the samples. Tables 1 and 2 below demonstrate the results of these tests.

TABLE 1

Buffered vs. Unbuffered Developer
with Regular "Hemoccult" Slides
Readings at 30 Seconds

| Sample pH | HEMOGLOBIN | | CIMETIDINE | |
|---|---|---|---|---|
| | Buffered Dev. | Unbuffered Dev. | Buffered Dev. | Unbuffered Dev. |
| 1.32 | 3 | 1 | 0 | 1 |
| 2.20 | 3 | 3 | 0 | 2 |
| 3.60 | 4 | 4 | 0 | 2 |
| 4.32 | 4 | 4 | 0 | 2 |
| 5.60 | 4 | 3 | 0 | 4 |
| 6.37 | 4 | 3 | 0 | 4 |

TABLE 2

Acidified vs. Unacidified Slides
with Buffered Developer

| | HEMOGLOBIN | | | | | | CIMETIDINE | | | | | |
|---|---|---|---|---|---|---|---|---|---|---|---|---|
| | Acid | | | No Acid | | | Acid | | | No Acid | | |
| | | | | | Reading Time (Min.) | | | | | | | |
| Sample pH | 0.5 | 2 | 5 | 0.5 | 2 | 5 | 0.5 | 2 | 5 | 0.5 | 2 | 5 |
| 1.32 | 2 | 5 | 5 | 3 | 5 | 5 | 0 | 0 | 0 | 0 | 0 | 0 |
| 5.60 | 5 | 5 | 5 | 5 | 5 | 5 | 0 | 0 | 0 | 0 | 1 | 5 |
| 6.37 | 5 | 5 | 5 | 4 | 5 | 5 | 0 | 0 | 0 | 0 | 3 | 5 |

"Hemoccult" slides were acidified by treating the center of the guaiac paper with 25 μl. of 0.1M citric acid. The paper was allowed to dry in ambient condition before using. The buffered developer contained hydrogen peroxide in a 0.2M citric acid/citrate buffer having a pH of 5.8. The unbuffered developer was the commercial "Hemoccult" developer comprising hydrogen peroxide in ethanol and water.

The blue color intensity was graded in a range of 1 to 5 with zero being colorless. It will be noted from Table 1 that the use of buffered developer on the regular "Hemoccult" slide produces a more consistent hemoglobin positive test. The buffered developer also eliminated the false positive tests caused by cimetidine. The results of Table 2 demonstrate that the use of acidified guaiac paper coupled with buffered developer will not produce a false positive result due to cimetidine even when the test readings were delayed and done after the prescribed 30 seconds. It will be noted that this treatment did not interfere with the test for hemoglobin.

The peroxidase catalyzed false positive reaction is also pH dependent, catalysis decreases with decreasing pH. It was discovered that acid treatment of the guaiac paper prior to sample application prevents a false-positive reaction catalyzed by acid-labile peroxidases. The treated paper, when used with a buffered developer, will produce a blue color with hemoglobin containing samples and will not interfere with the test for hemoglobin. For example, synthetic gastric fluid pH 6.5 containing purified horseradish peroxidase [2 units per ml.] when tested with "Hemoccult" slides gave false positive results. When the guaiac paper was pre-treated with acid and the above synthetic gastric fluid with peroxidase was applied and allowed to react with the acid for five minutes before developing, the blue positive color was not produced.

Acids found effective for the treatment of the guaiac paper were hydrochloric, sulfuric, citric, phosphoric and oxalic. Other strong organic and inorganic acids may be used. A preferable formula and method for the acid treatment of the guaiac paper is as follows:

| Solution I | | |
|---|---|---|
| Guaiac | | 7.8 gms. |
| Isopropanol | | 92.2 gms. |
| | Solution II | |
| Solution I | | 800 gms. |
| Citric Acid | | 768 gms. |
| Isopropanol | | 432 gms. |
| Water | | 300 gms. |

Solution II may be applied to the absorbent paper either by impregnation or printing.

The developer may be buffered with any well known buffering system such as, for example, citric acid/sodium citrate, citric acid/dibasic sodium phosphate, tris-maleate or EDTA.

The buffered developing solution will preferably contain from about 1% to about 5% hydrogen peroxide. The following buffered developer which is a 0.2M. citric acid/citrate buffer having a pH of 5.8 has been advantageously employed in this invention.

| Hydrogen Peroxide | 2.17 gms. |
|---|---|
| Ethanol | 32.87 gms. |
| Citric Acid | 0.75 gms. |
| Sodium Citrate | 4.37 gms. |
| Water | 58.80 gms. |
| Triton X-100 | 1.04 gms. |

Preferably a nonionic detergent is added to the buffered developer in order to assist in the peroxidase inhibition. Most advantageously a Triton X detergent, polyethylene glycol p-isooctylphenyl ether, is employed.

When a buffered developer is applied to the substrate of acid treated guaiac paper a specimen test slide results which is stable and permits testing for the presence of occult blood in specimens having a low pH such as gastric fluid. Further, false positive results due to cimetidine, peroxidases and metal ions such as copper and iron are eliminated.

Advantageously the specimen test slide of this invention will also include a pH test area. It is well known that intensive care patients whose gastric juice pH measures below 4 are often placed on medication, such as antacids to neutralize the acidity, or cimetidine to inhibit the gastric acid secretion. It is therefore important that the pH be determined rapidly. The pH test area present on the slide permits convenient, fast and reliable measurements of pH, in particular measurements of pH below 4.

The pH indicator is a mixture of dyes that change color with changes in hydrogen ion concentration. Any commercially pH indicator such as Micro pHydrion may be employed. Preferably, the mixture of dyes found effective for accurate measurement of pH under 4 is as follows:

| Bromophenol Blue, Sodium Salt | 1.50 gms. |
|---|---|
| Cresol Red Sodium Salt | 6.00 gms. |
| 2,6-Dichloroindophenol, Sodium Salt | 0.75 gms. |
| Metanyl Yellow | 0.75 gms. |
| Polyethylene Glycol | 200.00 g. |
| Purified Water, Distilled | 500.00 ml. |
| Isopropyl Alcohol | 500.00 ml. |

The dyes are added to a mixing vessel containing the water and alcohol and stirred until the solids are dissolved. The polyethylene glycol is then added and mixed until all the materials are dissolved. The above pH indicator liquid is then printed on the substrate or test strip.

Any standard pH Color Comparator well known to the art can also be placed on the slide in order to compare the color obtained in the pH test area to the pH Color Comparators that are thus provided on the slide.

The slide of this invention also includes an area having built-in or on-slide positive and negative performance monitors. The purpose of the monitors is to give an indication of the proper performance of the test system. The positive monitor contains a printed spot of a blood component that reacts to environmental conditions in a manner similar to hemoglobin. The negative monitor positioned adjacent the positive monitor is blank, an exposed area of the unmodified guaiac treated paper. Advantageously, the monitors may be highlighted by framing the positive and negative monitors with a brightly colored inert border.

If the guaiac test paper and the developer are operating properly, the monitor printed with the blood component will turn blue while the monitor that has not been modified will remain white when a drop of developing solution is added. Failure of the monitor printed with the blood component to turn blue would indicate that the blood-guaiac-developer reaction is not occurring, so that any negative result in the test would be suspect. Further, failure of the unmodified area to remain white would indicate that something in the test paper other than occult blood in the specimen was causing the guaiac-developer reaction to produce a blue color and that, therefore, any positive result in the test would be suspect.

A detailed description and better understanding of this invention can be had by referring to the accompanying drawings which show a preferred embodiment of the present invention.

FIG. 1 is a perspective view of the slide in an open position.

FIG. 2 is an enlarged fragmentary plan view of the slide shown in FIG. 1.

FIG. 3 shows an additional modification of FIG. 2.

Referring to FIG. 1 and FIG. 2 the slide 10 has a cover 12 and inner panel 16. Cover 12 has a locking tab 14 which is adapted to pass through locking flap 18 in panel 16 to lock the cover in a closed position.

Panel 16 has an opening 24 which contains the occult blood test area for gastric juice 26 and performance monitors 28. Panel 16 further contains pH test area 20 and Color Comparator Scale 22.

FIG. 3 shows a modification of FIG. 2 wherein panel 16 has the pH Color Comparator Scale printed on tear off flap 30 which covers monitors 28.

To use the slide, the technician separates the cover 12 from panel 16 and applies one drop of gastric sample to the pH test area and one drop to the occult blood test area. The pH of the sample is determined by visual comparison of the pH test area to the pH Color Comparator Scale. Two drops of the buffered developer are then added directly over the sample and one drop of developer between the positive and negative performance monitors. The development of any blue color in the occult blood test area after addition of developer is regarded as a positive result.

In the modified slide of FIG. 3, after the results are determined, tear off flap 30 is removed to expose the monitors 28. A drop of developer is then applied between the monitors to determine the performance of the test system.

The above embodiments are illustrative and are not intended to be limiting.

What is claimed is:

1. A method of testing for occult blood in gastric fluid which comprises applying the gastric fluid to an unbuffered acid treated absorbent substrate containing guaiac as a reagent and applying a buffered developing solution to said substrate and observing if the substrate is colored blue.

2. The method of claim 1 wherein the developing solution contains hydrogen peroxide.

3. A specimen test slide for testing occult blood in gastric fluid comprising a panel having one or more openings, an unbuffered acid treated absorbent test strip containing guaiac underlying said panel and extending under said openings for the reception of a specimen, a pH test area on a portion of the test strip underlying one of said openings, a pH Color Comparator Scale located on said panel to compare the color obtained in the pH test area to the Comparator, an occult blood test area and performance monitors printed on a portion of the test strip underlying another of said openings, a hinged cover adapted to overlie a portion of the panel and cover said openings and locking means thereon to lock the cover in a closed position.

4. The test slide of claim 3 in which the Color Comparators are printed on a tear off flap which covers the performance monitors.

5. The test slide of claim 3 in which the pH test area is printed on the test strip.

6. A test kit for determining the presence of occult blood in gastric fluid which comprises the slide of claim 3 and a receptacle containing a buffered developing solution which reacts with the guaiac to color the test strip blue.

* * * * *